(12) United States Patent
Monti (10) Patent No.: US 8,917,100 B2
(45) Date of Patent: Dec. 23, 2014

(54) DETECTING AND COUNTING DEVICE FOR DETECTING A WHOLENESS AND FOR COUNTING PHARMACEUTICAL/PARAPHARMACEUTICAL ARTICLES

(71) Applicant: Marchesini Group S.p.A., Pianoro (Bologna) (IT)

(72) Inventor: Giuseppe Monti, Pianoro (IT)

(73) Assignee: Marchesini Group S.p.A., Pianoro (Bologna) (IT)

( * ) Notice: Subject to any disclaimer, the term of this patent is extended or adjusted under 35 U.S.C. 154(b) by 112 days.

(21) Appl. No.: 13/864,618

(22) Filed: Apr. 17, 2013

(65) Prior Publication Data

US 2013/0271162 A1 Oct. 17, 2013

(30) Foreign Application Priority Data

Apr. 17, 2012 (IT) ................. B02012A0210

(51) Int. Cl.
| | | |
|---|---|---|
| G01R 27/26 | (2006.01) | |
| B65D 1/09 | (2006.01) | |
| G07F 11/00 | (2006.01) | |
| G01N 27/22 | (2006.01) | |
| B65B 57/10 | (2006.01) | |
| B65B 57/20 | (2006.01) | |
| G01N 33/15 | (2006.01) | |
| B65B 5/10 | (2006.01) | |

(52) U.S. Cl.
CPC ............. *G01N 27/22* (2013.01); *B65B 57/10* (2013.01); *B65B 57/20* (2013.01); *G01N 27/226* (2013.01); *G01N 33/15* (2013.01); *B65B 5/103* (2013.01)
USPC .............. 324/671; 324/71.4; 206/528; 221/7

(58) Field of Classification Search
CPC ........ B65B 57/10; B65B 57/20; B65B 5/103; G01B 7/087; G01N 27/22; G01N 27/221; G01N 27/226; G01R 27/02; G01R 27/26; G01R 27/2605; G06K 9/0002
USPC ................ 324/671, 663, 658, 649, 600, 71.4; 206/528, 534; 221/4, 7, 13, 96, 97, 200
See application file for complete search history.

(56) References Cited

U.S. PATENT DOCUMENTS 6,561,377 B1 * 5/2003 Pearson et al. .................... 221/7
7,956,623 B2 * 6/2011 Bassani et al. ................ 324/663
(Continued)

FOREIGN PATENT DOCUMENTS

| EP | 2048082 A | 4/2009 |
|---|---|---|
| WO | WO2008098340 A | 8/2008 |

OTHER PUBLICATIONS

European Search Report for Corresponding EP application No. 13 16 3273, dated Jun. 28, 2013, 3 pages.

*Primary Examiner* — Hoai-An D Nguyen
(74) *Attorney, Agent, or Firm* — William J. Sapone; Ware Fressola Maguire & Barber LLP (57) ABSTRACT

A detecting/counting device for pharmaceutical/parapharmaceutical articles has a sliding support groove (15) having a first lateral wall (15A) and a second lateral wall (15B) and a bottom. A first capacitive sensor (C1) has a first armature (C1A) parallel to the first lateral wall (15A) and a second armature (C1B) parallel to the second lateral wall and connected to a first reference potential Vref1 by a first circuit (O1). A second capacitive sensor (C2) has a first armature (C2A) parallel to the first lateral wall and a second armature (C2B) parallel to the second lateral wall and connected to a second reference potential Vref2 by a second circuit (O2). A data processing unit (E) receives signals from the first circuit and the second circuit during transit of an article, indicating the shape of the articles, and compares them with reference ranges to determine whether the article is whole.

9 Claims, 6 Drawing Sheets

(56) References Cited

U.S. PATENT DOCUMENTS

| | | |
|---|---|---|
| 7,999,541 B2* | 8/2011 | Chisholm et al. ............. 324/300 |
| 8,020,724 B2* | 9/2011 | Remis et al. .................. 221/211 |
| 8,102,170 B2* | 1/2012 | Monti .......................... 324/71.4 |
| 8,121,392 B2* | 2/2012 | Popovich et al. ............. 382/143 |
| 2009/0056825 A1 | 3/2009 | Mertens |
| 2013/0092592 A1* | 4/2013 | Singer .......................... 206/528 |

* cited by examiner

DETECTING AND COUNTING DEVICE FOR DETECTING A WHOLENESS AND FOR COUNTING PHARMACEUTICAL/PARAPHARMACEUTICAL ARTICLES

FIELD OF THE INVENTION

The present invention relates to the technical sector concerning the filling of containers, such as for example bottles, with pharmaceutical/parapharmaceutical articles such as for example pills, tablets, capsules etc.

DESCRIPTION OF THE PRIOR ART

In this specific sector, when discrete articles of a pharmaceutical/parapharmaceutical type are to be packed, such as for example, as mentioned above, pills, tablets, capsules etc., in a container, such as for example a bottle, it is of fundamental importance to carry out a recognition of the wholeness of the articles before they reach the packing zone where the articles are directed to inside the container.

It is necessary to prevent not perfectly-whole articles, i.e. articles that are partly damaged or grazed, or articles that do not corresponding to required standards, from entering into commercial situations.

The possibility of carrying out this control, i.e. an operation that controls, or validates, the integrity of the article before it is placed internally of a relative container, can enable carrying out a discriminatory selection, i.e. can distinguish whether an article is suitable or not, i.e. whole or not whole, to be placed on the market.

It is further of fundamental importance that inside each single container destined for sale to the public there should be the exact number of articles requested. For this reason, it is necessary to be able to succeed in carrying out the counting of the articles which are effectively directed internally of the container.

For the above purposes and needs (evaluation of the integrity of the articles directed towards the container with validation of the integrity thereof, counting the articles validated as whole and placed internally of a container), the use of detecting and counting devices is known which are specially predisposed in the automatic packing machines of the pharmaceutical/parapharmaceutical articles with the aim of carrying out the detecting of the wholeness (detection of the shape) of the articles, and the counting thereof, before they can reach the destined zone for being directed into the containers.

The automatic packing machines of pharmaceutical/parapharmaceutical articles, such as for example pills, tables, capsules, etc., are provided with a hopper, in which the articles are loosely piled, which articles will then be placed in the containers, and a series of vibrating conveyors which receive the articles falling from the hopper such as to convey them, spacing them from one another, towards the part of the machine dedicated to inserting them into the containers.

The vibrating conveyors include a series of V-shaped grooves flanked to one another, where in each of the V-shaped channels the articles that have fallen from the hopper are advanced in a line one behind another, and, thanks to the vibrating motion, in such a way that they are separated and distanced from one another.

In the section of the machine dedicated to insert the articles in the containers, a series of article-accumulating conduits are usually present, each of which can receive the articles that have exited from a corresponding V-groove of the vibrating conveyors, and retain them with a mobile hatch door before allowing them to fall into an underlying container when the required number of articles has been reached.

Detecting and counting devices are therefore usually positioned in a location between the outlet of the V-shaped vibrating conveyors and the inlet of the accumulating conduits, which are situated above the containers to be filled.

Detecting and counting devices are known which use a capacitive sensor, i.e., capacitor plates, for carrying out the detecting of the shapes of the articles.

For example, document US2009/056825 discloses a detecting and counting device which uses a capacitor provided with two armatures which are arranged such that the two armatures are positioned along the drop path of the articles that have exited from a groove of the vibrating conveyors towards the underlying accumulating conduit of products, or container.

In particular, the capacitor is arranged such that the falling articles pass between the two armatures. In this way, at each falling passage of an article between the two armatures of the capacitor, the signal emitted by the capacitor will be indicative of the shape of the article that has transited. This signal is compared with reference values for evaluating whether the article is more or less whole and conforming to the required parameters.

In a case in which it is found that the article is not whole or conforming, a blower nozzle is present, which directs a jet of air towards the falling path of the article with the intention of deviating it from its normal fall path.

The use of a device made in this way does not however guarantee that internally of the container, which will then be placed on the market, there will exclusively be perfectly whole articles.

In fact, the articles must fall freely by gravity in order to be able to transit through the armatures of the capacitor and thus are liable to impacts or bounding of relevant entities when they arrive in the accumulating conduits which can lead to breakage or grazing.

It is therefore not rare for an article that has been validated as whole following the passage thereof through the capacitive sensor to be subjected to impacts which can cause damage and be in any case inserted internally of the container, and that therefore the container can be placed on the market notwithstanding the presence of one or more non-whole articles in it, which therefore do not conform to required standards.

Figure 1:
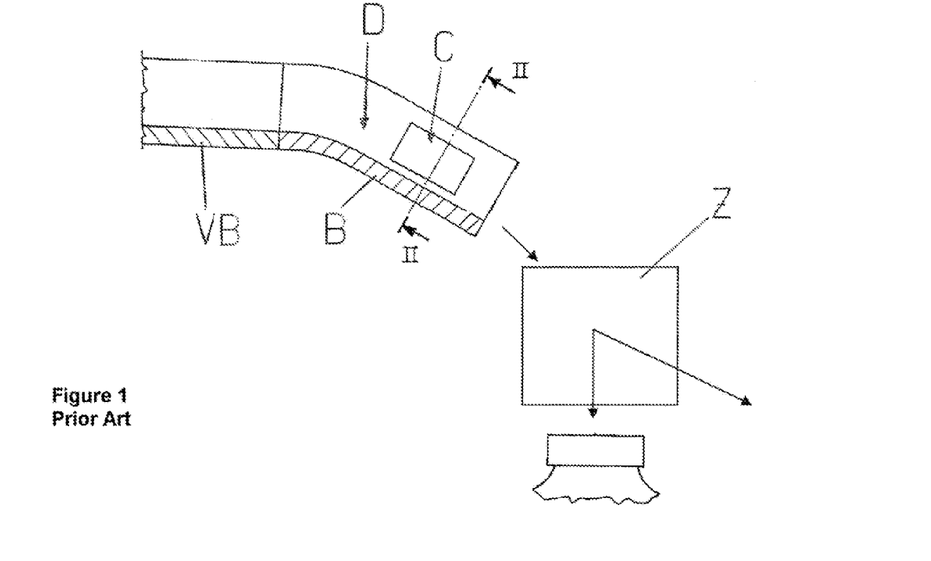
FIG. 1, already mentioned herein above, illustrates a lateral view in vertical section of a detecting and counting device used in the prior art for detecting the integrity and counting pharmaceutical/parapharmaceutical articles in automatic packing machines, which device is positioned at the outlet of the vibrating conveyors (Vb) and upstream of the direction section (Z) of the articles towards the containers.

Another known device which uses a capacitive sensor, i.e. a capacitor, for detecting the integrity of the pharmaceutical/parapharmaceutical articles, is illustrated in FIG. 1.

This device comprises a support (B) for sliding of products which exhibits at least a V-shaped groove (D) which is arranged immediately downstream of the V-shaped vibrating conveyors of the packing machine, and upstream of the section (Z) dedicated to directing the articles towards the containers to be filled, such that the groove (D) of the device is arranged consecutively to a V-shaped groove of the vibrating conveyors (VB) of the packing machine.

This device further comprises a capacitive sensor (C), provided with two armatures (Ca, Cb) which are arranged with respect to the support (B) in such a way that the two armatures (Ca, Cb) are facing and parallel to the two lateral walls of the V-shaped groove.

Figure 2A:
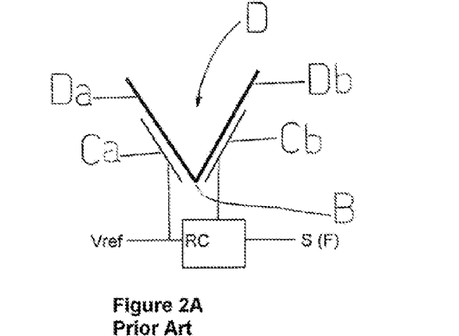
FIG. 2A illustrates the view along section II-II of FIG. 1, and illustrates the arrangement of the capacitor in the prior-art device with respect to the walls of the sliding groove of the articles and the electronic oscillator circuit RC of which the capacitor is a part.
Figure 2B:
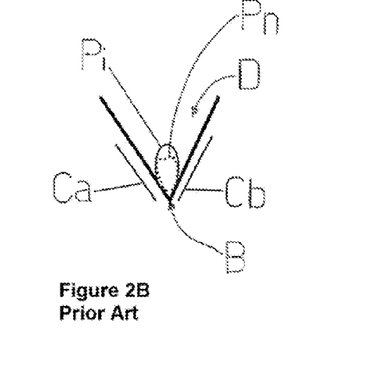
FIG. 2B illustrates the same view as in FIG. 2A, with the presence of a whole article, in an unbroken line, which is sliding along the groove (D) in a central position and is crossing the two armatures of the capacitor, and the presence of a non-whole article, i.e. defective as lacking a part thereof, in broken line, also in transit across the armatures of the capacitors in the central position.

As can clearly be seen in FIGS. 2A, 2B, which are viewed along section plane II-II of FIG. 1, the capacitive sensor (C) is arranged, with respect to the support (B), in such a way that a first armature (Ca) is facing and parallel to a first lateral wall (Da) of the groove (D) and a second armature (Cb) is facing and parallel to the second lateral wall (Db) of the groove (D).

According to the number of V-shaped grooves present in the vibrating planes (Vb), the support (B) of the device will have a corresponding number of V-shaped grooves (D) and a corresponding number of single capacitors for each of the grooves. Each single capacitive sensor is associated to a relative groove (D) as illustrated in FIGS. 1, 2A, 2B.

The known device also has an electronic circuit, or RC oscillator for each of the capacitors present for each groove (D), and each RC oscillator is connected to the capacitor (C) as illustrated in FIG. 2A. The first armature (Ca) of the capacitor is connected to a reference potential Vref, which also constitutes the input to the oscillator circuit RC.

With this arrangement of the capacitor (C) and the use of the RC oscillator circuit it is possible to have, in output from the RC oscillator circuit, a signal S(F) in the frequency F. The wave form of the signal S(F) in frequency F as a function of time T is therefore indicative of the value of the dielectric capacity interposed between the two armatures (Ca, Cb) of the capacitor (C).

Figure 3A:
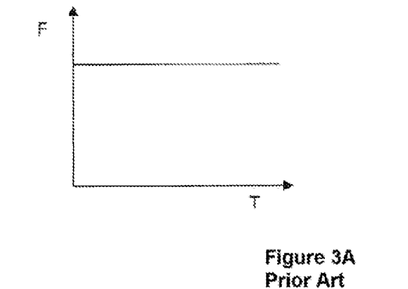
FIG. 3A illustrates the progression of the output signal from the oscillator circuit in a moment in which there is no article in transit between the two armatures of the capacitor of the prior-art device.

FIG. 3A illustrates the signal S(F) in frequency F, as a function of time T, at the output of the RC oscillator circuit when no article transits across the capacitor (C) along the groove (D) of the support (B) of the detecting and counting device of the prior art.

The passage of an article across the armatures of the capacitor (C) determines, on the other hand, a variation in the dielectric constant of the dielectric between the two armatures (Ca, Cb} which is translated into a perturbation of the signal S(F) in frequency (F) in output from the oscillator circuit RC, for the time required by the article to cross the armatures (Ca, Cb) of the capacitor (C).

The wave form of the output signal S(F) will be different according to the shape, dimension and mass of the article transiting between the two armatures (Ca, Cb).

Figure 3B:
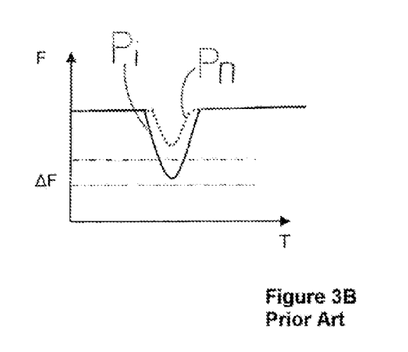
FIG. 3B illustrates the progression of the output signal from the oscillator circuit of the prior-art device of FIG. 1, respectively in a case of a passage between the armatures of the capacitor of a whole article (unbroken line) and a non-whole article (broken line)

For example, FIG. 2B illustrates the case of passage between the armatures of the capacitor of a whole table (unbroken line) and a non-whole tablet, as it is grazed or chipped or partly broken (broken line) while FIG. 38 represents the relative output signals of the oscillator.

The signals that fall within a suitability range AF, predetermined precedingly on the basis of a series of sample detections performed on whole articles, would therefore be indicative of whole articles, while signals falling beyond this range would be indicative of defective articles and which therefore must be rejected and not directed into the containers.

In this regard, the second (Z) of the packing machine for directing the articles towards the containers is provided with special deviating means which switch the articles for which a non-whole signal has been received towards a reject section.

The use of a device like the one described above has not however provided optimal results for all the possible type and shapes of tablets, pills or capsules, for the following reasons.

It has been observed that the signal provided in output from the oscillator circuit can vary according to the orientation the article has as it passes across the two armatures (Ca, Cb) of the capacitor (C).

It has been determined that the perturbation of the base signal of FIG. 3A (absence of passage) is less intense the closer the article passes to the armature (Ca) of the capacitor (C) which is connected to the reference potential Vref, while the perturbation of the signal is more intense the closer the article passes to the other armature (Cb) of the capacitor.

Thus, in a case in which the articles to be inserted in the containers exhibit a substantially spherical transversal section or in any case such that all the articles to be controlled maintain, once having fallen from the vibrating V conveyors in the groove (D) of the support (B), always a same orientation during the sliding thereof in the groove (D) and across the capacitor, the known device provides satisfactory results as the perturbations of the output signal from the oscillator circuit caused by the passage of whole articles will always be distinguishable from those caused, on the other hand, by the passage of non-whole articles, being broken, grazed or the like.

Figure 2C:
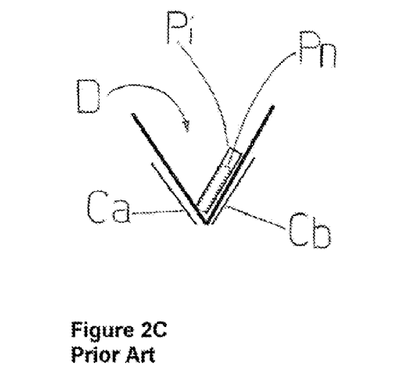
FIGS. 2C, 2D and 2E illustrate the various possible orientations and positions which the articles, whole (unbroken line) and non-whole (broken line), can assume when sliding along the groove (D) of the prior-art device.
Figure 2D:
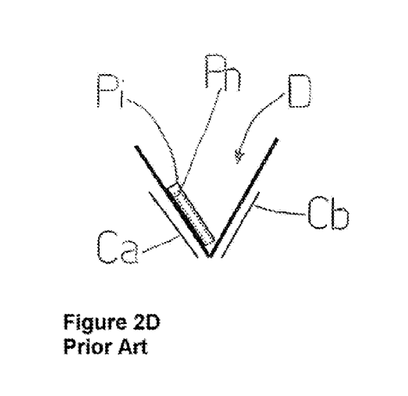
Figure 3C:
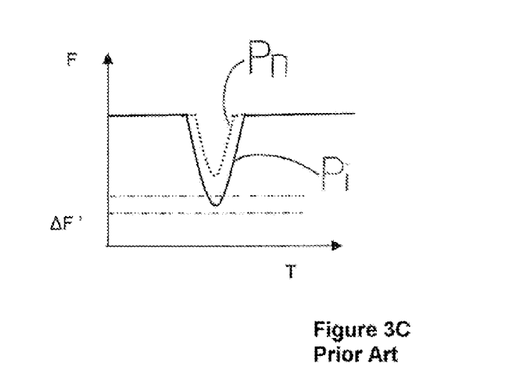
FIGS. 3C, 3D and 3E illustrate the progressions of the output signal from the oscillator circuit of the prior-art device respectively in the situations illustrated in FIGS. 2C, 2D and 2E.
Figure 3D:
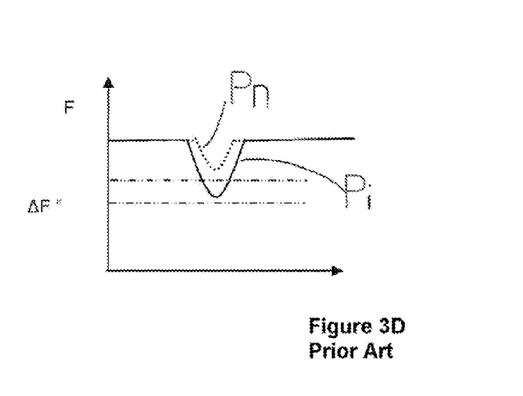

In this regard see for example FIG. 2C and FIG. 3C which represent the situation in which all the articles slide across the capacitor (C), always resting on the right wall (Db) of the groove (D) (in these two figures the continuous line indicates a whole article (Pi), the broken line indicates and article (Pn) that is not whole as it has been broken or grazed), and also FIG. 2D and FIG. 3D which represent the situation in which all the articles slide across the capacitor (C) always resting on the left wall (Da) of the groove (D) (in these figures too the continuous line indicates a whole article (Pi), the broken line a non-whole article (Pn) as it is broken or grazed).

It has been found that the known device does not however provide satisfactory results when the shape of the article is such that it is not possible to know with certainty if once having passed from the vibrating V-conveyors in the groove (D) of the support (8), the articles will all slide in the center of the groove (D), or always resting on one wall or always resting on the other wall.

In fact, when the articles have such a shape that for example the diameter is very much greater than the height, it is not possible to know whether these articles, once having passed from the vibrating conveyors to the V-groove (D) of the detecting and counting device, will slide restingly on the right lateral wall (Cb) or the left lateral wall (Ca).

It has been found that in a case In which a whole article (Pi) slides in the groove (D) of the support (B) resting on the left wall (Da) to which the armature (Ca) is associated, which armature is connected to the reference potential Vref, the perturbation of the output signal of the oscillator circuit is comparable to the perturbation of the signal which is given by the transit of a non-whole article (Pn), which on the other hand slides in the groove (D) resting on the right wall (Db) to which the other armature (Cb) of the capacitor is associated.

Figure 3E:
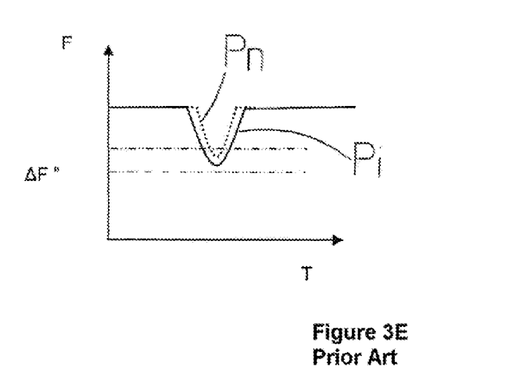

FIG. 3E illustrates this situation as encountered by the Applicant, where the two signals in output, the one represented in a continuous line, for the whole article (Pi), and the one represented in a broken line, for the non-whole article (Pn), are comparable to one another.

In this situation, therefore, in the case of a passage of a non-whole article, there would be an output signal which would fall within the suitability range, and thus would lead to the directing of the non-whole article internally of the container.

It has been further found that this known device of FIG. 1 does not provide entirely satisfactory results even in a case in which the articles are constituted by the type of tablets known as oblong, i.e. those tablets which contain antibiotics as active ingredient and which have a substantially rectangular section, having dimensions that are notably greater than those of the classic tablets and which usually exhibit a pre-fracture line which enables them to be broken in half so as to facilitate the administration of, or regulate the dose to be taken.

In fact, it can happen that these tablets can break along the pre-fracture line before reaching the detecting device, for example when piled in the hopper or during the fall thereof onto the vibrating conveyors.

A tablet broken in half always exhibits the same transversal section as a whole tablet and the longitudinal dimensions of it are in any case significant. This means that the passage of a half-tablet across the two armatures (Ca, Cb) of the capacitor (C) leads to a perturbation of the signal in output from the RC oscillator circuit that is comparable to the perturbation given by the passage of a whole tablet.

Consequently, in this case too the known device will not be able to provide a precise datum on the effective nature of the tablets which have transited along the groove (D) and which have passed across the armatures (Ca, Cb) of the capacitor (C).

SUMMARY OF THE INVENTION

The aim of the present invention is therefore to provide a new detecting and counting device, for detecting the integrity and the count of the pharmaceutical/parapharmaceutical articles, able to obviate the various drawbacks mentioned above in relation to the prior art.

In particular the aim of the present invention is to provide a detecting and counting device, to be used In automatic machines for packing the pharmaceutical/parapharmaceutical articles internally of relative containers, in a position upstream of the directing zone of the articles towards the containers, able to supply a precise datum on the nature of these articles, and their number, before they reach this zone, thus enabling directing of only the articles recognized effectively as whole into the containers.

In this way, the containers will be filled only with whole articles, and only with the required number of articles.

This aim is attained by a detecting and counting device for detecting a wholeness of and for counting pharmaceutical/parapharmaceutical articles, the device being usable in automatic machines for packing pharmaceutical/parapharmaceutical articles internally of relative containers of a type comprising vibrating conveyors for advancing the articles in line, distanced from one another, and a directing zone for directing the articles towards containers, for filling the containers. The device has a sliding support for sliding the articles, exhibiting an article inlet side and an article outlet side. The sliding support is positionable in the machines in a position downstream of the vibrating conveyors and upstream of the article directing zone in such a way that the article inlet side is arranged consecutively to the outlet of the vibrating conveyors, so as to receive therefrom one article after another. The article outlet side faces towards the initial part of the directing zone. The sliding support comprises at least one groove for sliding the articles from the inlet side to the outlet side, and has a bottom, a first lateral wall and a second lateral wall, exhibiting a shape in transversal section that is such that the first lateral wall and the second lateral wall converge towards a bottom of the channel.

A first capacitive sensor having a first armature and a second armature is positioned with respect to the groove in a first position and orientated in such a way that the first armature is arranged parallel to the first lateral wall of the groove and the second armature is arranged parallel to the second lateral wall of the groove.

A first electronic circuit is connected to a first reference potential Vref1, with the first capacitive sensor being a detecting component of the first circuit. The first armature of the first capacitive sensor is electrically connected to the first reference potential Vref1, the first circuit emitting a first signal S1(F) in output that is a function of the variation of the capacitive value of the first capacitive sensor following a transit of an article between the armatures thereof and indicating the shape of the article that has transited.

The device further includes a second capacitive sensor which has a first armature and a second armature, the second capacitive sensor being positioned with respect to the groove in a second position, located between the position of the first capacitive sensor and the outlet side, and orientated in such a way that the first armature is arranged parallel to the first lateral wall of the groove and the second armature is arranged parallel to the second lateral wall of the groove.

A second electronic circuit is connected to a second reference potential Vref2, the second capacitive sensor being a detecting component of the second circuit, the second armature of the second capacitive sensor being parallel to the second lateral wall of the groove and being electrically connected to the second reference potential Vref2. The second circuit emits a second signal S2(F) in output that is a function of the variation of the capacitive value of the second capacitive sensor following transit of an article between the armatures and indicating the shape of the article that has transited.

A data processing unit is connected to the first circuit and to the second circuit for receiving the first signal S1(F) and the second signal S2(F), the data processing unit being configured to process the first signal S1(F) and the second signal S2(F) by singly comparing them to corresponding reference intervals indicative of whole articles, and supplying a datum relative to the wholeness of the article that has transited between the two capacitive sensors only when the first signal S1(F) and the second signal S2(F) both fall within the respective reference ranges.

Other advantageous characteristics of the device of the present invention will be further discussed below.

As indicated above, the detecting and counting device of the present invention is specifically applicable in automatic packing machines for placing pharmaceutical/parapharmaceutical articles into containers.

These machines usually include a hopper where the articles are accumulated and piled loosely, a series of vibrating conveyors for conveying the articles, separating and spacing them one from another in a sequence, from the hopper towards the section of the machine provided for carrying out the filling of the containers.

The device of the present invention is installed in a position located downstream of the vibrating conveyors and in a position upstream of the section of the machine for carrying out the filling of the containers, where a deviator operates for directing the articles judged to be whole towards a series of accumulating conduits of the articles which are arranged vertically above an advancing line of the containers to be filled.

This device is therefore intended to detect the type of articles received by the vibrating conveyors and to supply a signal indicating the integrity thereof or the non integrity thereof, and correspondingly a signal indicating the number of articles recognized as whole, which signals can thus be usable for enabling the deviator, present downstream of the device, to direct only the whole articles towards the accumulating conduits such that in the conduits, and therefore in the containers, there are only whole articles, and in the correct required number.

BRIEF DESCRIPTION OF THE DRAWINGS

The characteristics of the detecting and counting device, for detecting the integrity and for the counting of the pharmaceutical/parapharmaceutical articles, disclosed by the present invention are described in the following with reference to the accompanying figures of the drawings, in which:

FIG. 5A represents a possible situation of transit of a whole article (unbroken line) and a non-whole article (broken line) across the first detecting component of the device of the invention, while

FIG. 6A illustrates the same transit situation as in FIG. 5A, of a whole article (unbroken line) and a non-whole article (broken line) across the second detecting component of the device of the invention, while

FIG. 7 illustrates, with reference to the first detecting component of the device of the invention, two possible positions and orientations assumed by whole articles in a step of calibrating the device, while

FIG. 8 illustrates, with reference to the second detecting component of the device of the invention, two possible positions and or orientations assumed by whole articles in a step of calibration of the device, while

DESCRIPTION OF PREFERRED EMBODIMENTS

With reference to the accompanying figures, reference number (100) denotes the detecting and counting device of the present invention which, as indicated above, is specifically applicable in automatic machines for packing of pharmaceutical/parapharmaceutical articles in relative containers.

Figure 4:
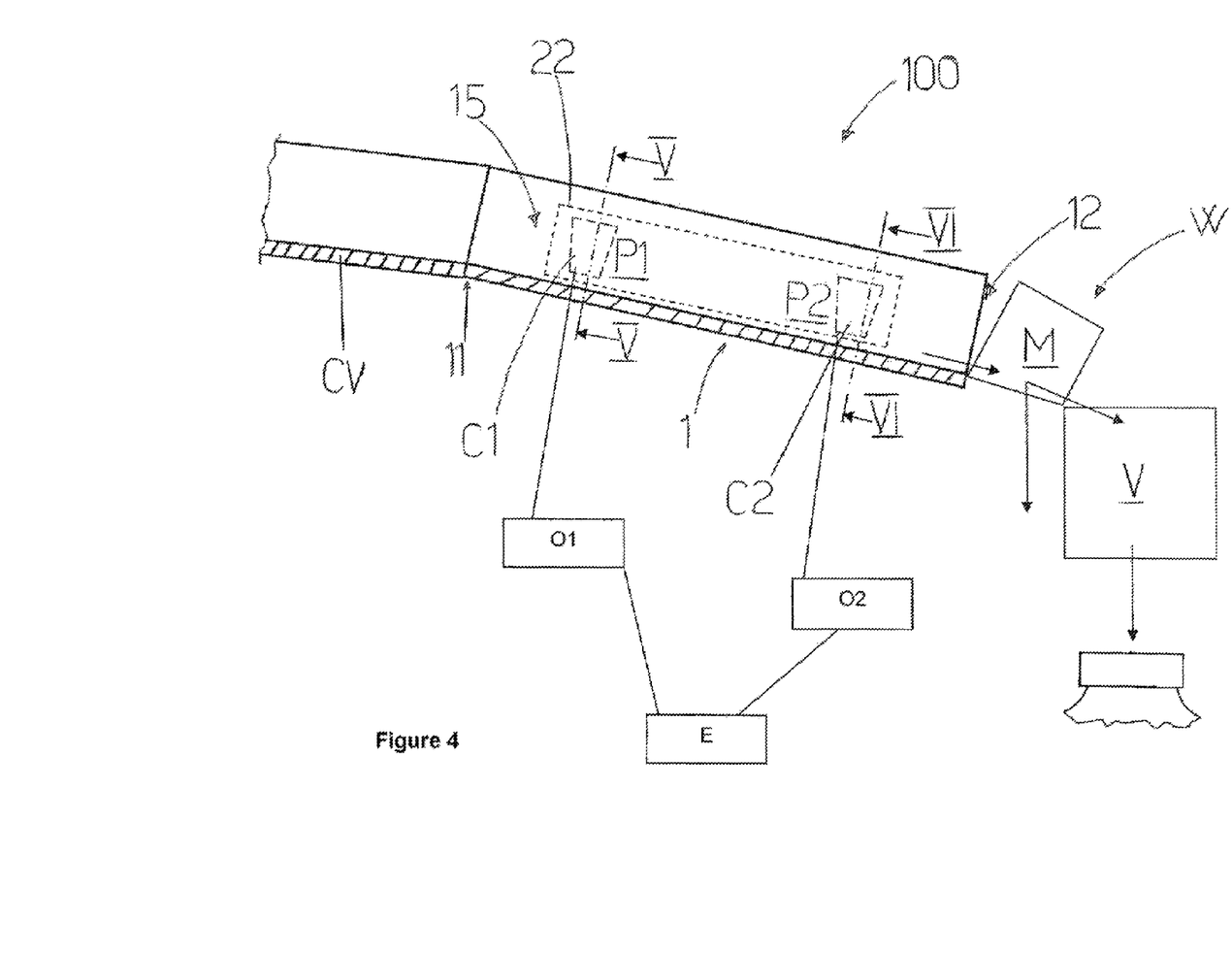
FIG. 4 is a lateral view in vertical section of the detecting and counting device of the invention which is installed and positioned in a position immediately downstream of the vibrating conveyors of an automatic packing machine for packing pharmaceutical/parapharmaceutical articles into containers, and upstream of a directing device for directing whole articles towards the container filling zone and for the rejecting non-whole articles.

The device (100) is installed and mounted in the machine, as illustrated in FIG. 4, in a positioned between the vibrating conveyors (CV) and the zone (W) in which the articles will be directed towards the containers to be filled.

The vibrating conveyors (CV) receive the articles from a hopper or magazine where the articles are stacked and stored; the task of the vibrating conveyors (CV) is to advance the articles towards the zones of the machine set aside for inserting the articles into relative containers in such a way as to distance them one from another.

The directing zone (W) of the articles towards the containers exhibits a director (M) (only schematically indicated in FIG. 4) for directing only the articles considered to be whole towards a series of accumulating conduits (V) (only schematically illustrated in FIG. 4) which are usually arranged above a double hopper provided with hatch doors for unloading and introduction of the articles into containers which are advanced along an advancement line (not illustrated).

The detecting and counting device (100) of the invention comprises a sliding support (1) for sliding of the articles, which exhibits an article inlet side (11) and an article outlet side (12).

The device (100) is predisposed in the packing machine of the articles in such a way that the sliding support (1) is positioned in a position downstream of the vibrating conveyors (CV) and upstream of the article directing zone (W) in such a way that the article inlet side (11) is arranged consecutively to the outlet of the vibrating conveyors (CV) so as to be able to receive therefrom one article after another, and the article outlet side (12) is facing towards the initial part of the directing zone (W).

The sliding support (1) comprises at least a groove (15) for sliding of the articles from the inlet side (11) to the outlet side (12), which exhibits a bottom, a first lateral wall (15A) and a second lateral wall (15B) which converge towards the bottom of the groove (15).

Figure 5:
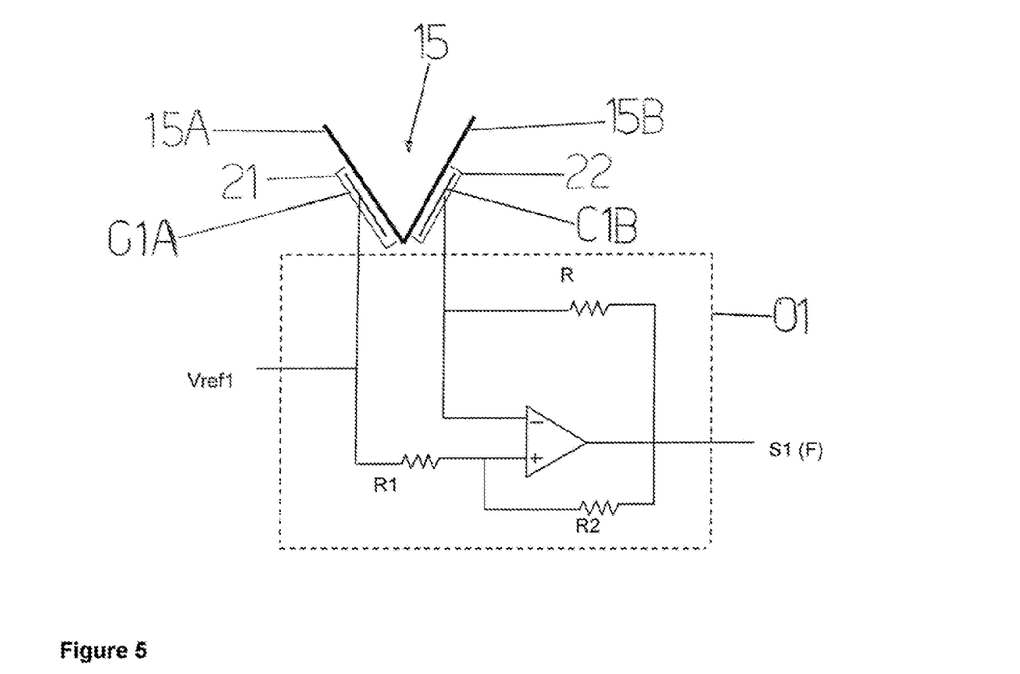
FIG. 5 illustrates the view of section V-V of FIG. 4 for illustrating a first detecting component of the device of the invention, together with the electrical diagram of a first electronic circuit of the device of the invention of which the first detecting component Is a part.
Figure 5A:
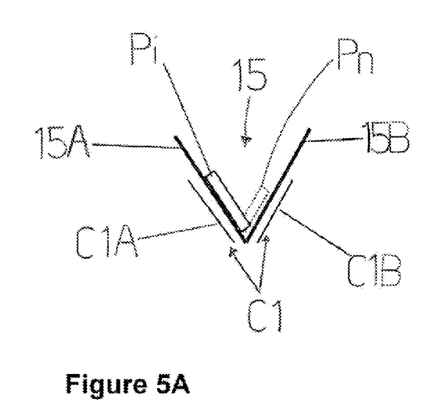

The device (100) comprises a first capacitive sensor (C1) having a first armature (C1A) and a second armature (C1B), the first capacitive sensor (C1) being positioned with respect to the groove (15) in a first position (P1) and orientated in such a way that the relative first armature (C1A) is arranged parallel to the first lateral wall (15A) of the groove (15) and the relative second armature (C1B) is arranged parallel to the second lateral wall (15B) of the groove (15) (see FIG. 5A which schematically illustrates the arrangement of the two armatures of the first capacitor (C1) with respect to the lateral walls of the groove 15).

The device (100) further includes a first electronic circuit (O1), preferably an RC oscillator such as for example illustrated in FIG. 5, which is connected to a first reference potential Vref1, the first capacitive sensor (C1) being a detecting component of the first circuit (O1) in such a way that the first armature (C1A) of the first capacitive sensor (C1) is electrically connected to the first reference potential Vref1.

This first electronic circuit (O1) is able to emit a first signal S1(F) in output that is a function of the variation of the capacity value of the first capacitive sensor (C1) following a transit of an article between the armatures thereof and indicating the shape of the article that has transited.

Figure 5B:
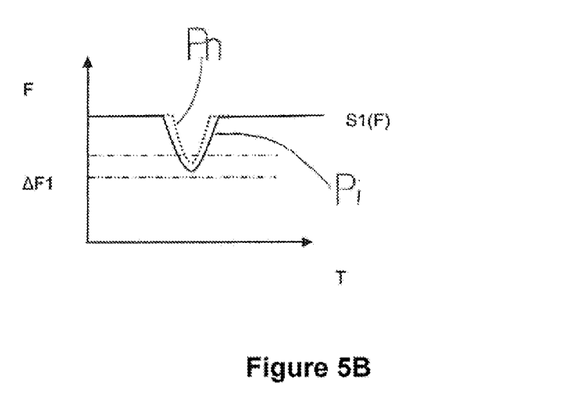
FIG. 5B represents the progression of the output signal of the first electronic circuit respectively for a case of a transit of the whole article (unbroken line) and a transit of the non-whole article (broken line)

In this regard, see for example FIG. 5B where an unbroken line represents the output signal S1(F) of the first circuit (O1) when a whole article (Pi) passes across the first capacitor (C1), the whole article (Pi) being rested on the first lateral wall (15A) of the groove (15), illustrated in an unbroken line in FIG. 5A, and also the output signal S1(F) is represented, illustrated in a broken line, of the first circuit (O1) when a non-whole article (Pn) crosses the first capacitor (C1), the non-whole article (Pn) being rested on the second lateral wall (15B) of the groove (15) and represented in a broken line in FIG. 5A.

A first peculiarity of the detecting and counting device (100) of the present invention consists in the fact that it comprises a second capacitive sensor (C2) having a first armature (C2A) and a second armature (C2B), the second capacitive sensor (C2} being positioned, with respect to the groove (15), in a second position (P2), which is located between the first position (P1) of the first capacitive sensor (C1) and the output side (12) (see FIG. 4).

Figure 6:
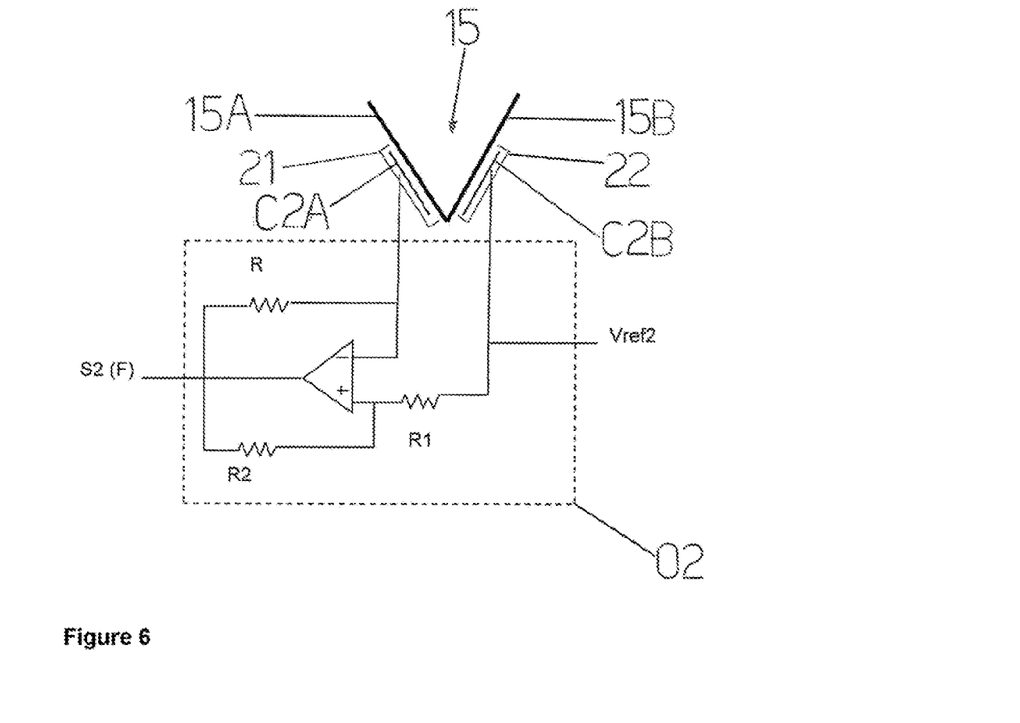
FIG. 6 illustrates the view of section VI-VI of FIG. 4 to illustrate a second detecting component of the device of the invention, together with the electrical diagram of a second electronic circuit of the device of the invention of which the second detecting component is a part.

The second capacitor (C2) is orientated in such a way that the first armature (C2A) thereof is arranged parallel to the first lateral wall (15A) of the groove (15) and the relative second armature (15B) is arranged parallel to the second lateral wall (15B) of the groove (15) (see FIG. 6).

A second peculiarity of the device (100) is constituted by the fact that it comprises a second electronic circuit (O2), preferably an RC oscillator such as for example as illustrated in FIG. 6, which is connected to a second reference potential Vref2, the second capacitive sensor (C2) being a part as a detecting component of the second circuit (O2) in such a way that the second armature (C2B) of the second capacitive sensor (C2), i.e. the armature that is parallel to the second lateral wall (15B) of the groove (15), is electrically connected to the second reference potential Vref2.

The second circuit (O2) supplies in output a second signal S2(F) that is a function of the variation of the capacitance value of the second capacitive sensor (C2) following transit of an article between the armatures and indicating the shape of the article that has transited.

Figure 6A:
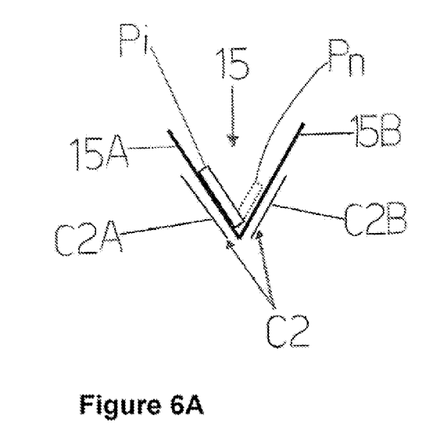
Figure 6B:
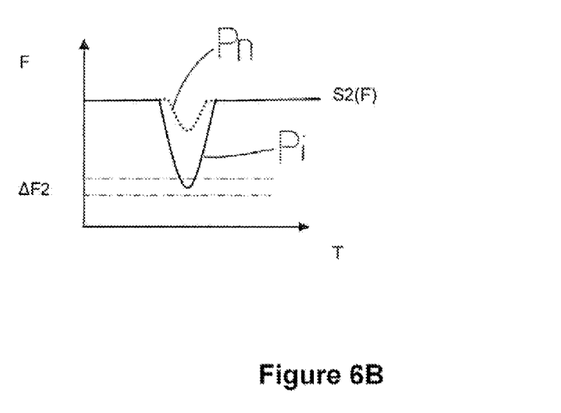
FIG. 6B represents the progression of the output signal of the second electronic circuit respectively for the case of transit of the whole article (continuous line) and transit of the non-whole article (broken line)

In this regard see for example FIG. 6B, where the output signal S2(F) of the second circuit (O2) is represented in an unbroken line when a whole article (Pi) passes across the second capacitor (C2), which whole article (Pi) is rested on the first lateral wall (15A) of the groove (15), illustrated in an unbroken line In FIG. 6A, and the output signal S2(F) is also represented, in a broken line, of the second circuit (O2) when a non-whole article (Pn) passes across the second capacitor (C2), the non-whole article (Pn) being rested on the second lateral wall (15B) of the groove (15), shown in a broken line in FIG. 6A.

The device (100) further comprises a data processing unit (E), connected to the first circuit (O1) and to the second circuit (O2) so as to be able to receive the first signal S1(F) from the first circuit (O1) and the second signal S2(F) from the second circuit (O2).

The data processing unit (E) is predisposed to process the first signal S1(F) and the second signal S2(F) by singly comparing them to corresponding reference intervals indicative of whole articles, and supplying a datum relative to the wholeness of the article that has transited between the two capacitive sensors only when the first signal S1(F) and the second signal S2(F) both fall internally of the respective reference ranges.

For example, reference is now made to FIGS. 5A, 5B, 6A, 6B which represent a situation in which a whole article (Pi) (unbroken line) slides along the groove (15) of the device (100) resting on the first lateral wall (15A) of the groove (15) while a following non-whole article (Pn) (broken line) slides along the groove (15) resting on the second lateral wall (15B) of the groove.

The first circuit (O1) emits in output the signal S1(F) illustrated in an unbroken line in FIG. 5B when the whole article (Pi) will pass the armatures (C1A, C1B) of the first capacitor (C1) while it will emit the signal S1(F) illustrated in a broken line in FIG. 5B when the non-whole article (Pn) will pass the armatures (C1A, C1B) of the first capacitor (C1).

The second circuit (O2) emits in output the signal S2(F) illustrated in an unbroken line in FIG. 6B when the whole article (Pi) will pass the armatures (C2A, C2B) of the second capacitor (C2) while it will emit the signal S2(F) illustrated in a broken line in FIG. 6B when the non-whole article (Pn) will pass the armatures (C2A, C2B) of the second capacitor (C2).

The data processing unit (E) which receives the output signals from the two circuits will process the two signals S1(F) and S2(F) corresponding to the passage of each article across the two capacitors (C1, C2), comparing them with respective reference ranges, respectively $\Delta F1$ and $\Delta F2$, indicative of the wholeness of the articles.

The processing unit (E) will supply a datum relating to a whole article only when both the signal S1(F) and the signal S2(F) both fall within the respective reference ranges $\Delta F1$ and $\Delta F2$.

This information can therefore be used by the deviator (M) present downstream of the device (100), i.e. present in the article-directing zone (W) towards the containers, so as to be positioned in such a location as to enable the article recognized as whole that has reached the outlet side (12) of the sliding support (1) to proceed in its travel up to reaching the accumulating conduits (V) and/or the containers.

The processing unit (E) in this case will use a counter indicating the number of whole articles which have been recognized and directed towards the accumulating conduit (V) and the containers.

In an opposite case, i.e. when at least one of the two signals does not fall internally of the respective reference intervals, the processing unit (E) with supply a non-whole article datum, and consequently the datum will be used by the deviator (M) to switch the article recognized as not whole, once it has passed the output side (12) of the sliding support (1) towards a discharge conduit.

In this way, thanks to the detecting and counting device (100) proposed by the present invention the containers will be filled only with whole articles and precisely with the requested number of articles.

Differently to known devices, for example the known device of FIG. 1, the device (100) of the invention therefore enables supplying precise information on the effective wholeness of the articles to be placed in the containers independently of the orientation that the articles assume during the transfer thereof from the vibrating conveyors to the directing zone towards the containers, across the support element and the relative groove.

Figure 2E:
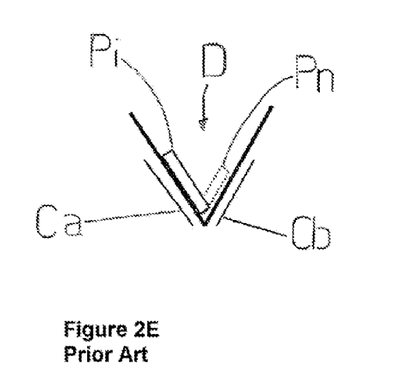

In fact, in the situation in which the whole article slides resting on one of a first wall of the groove and a non-whole article slides resting on the second wall of the groove, in the prior art device of FIG. 1 and FIG. 2E, this prior-art device would not be able to discriminate which between the two articles was effectively the whole one and which not, as the signals emitted by the circuit in both cases could be comparable to one another and therefore not distinguishable.

The device of the present invention, on the other hand, in the same situation and by virtue of the particular mode with which the two capacitive sensors (C1, C2) are inserted in the respective electronic circuits (O1, O2) and connected to the relative reference potentials Vref1, Vref2 (the first armature (C1A) of the first capacitive sensor (C1) parallel to the first lateral wall (15A) of the groove is connected to the reference potential while it is the second armature (C2B) of the second capacitive sensor (C2) parallel to the second lateral wall (15B) of the groove (15) that is connected to the reference potential) can have, for each article which slides along the groove (15), two signals at all times: a first signal S1(F) in consequence of the passage of the article across the first capacitive sensor (C1) and a second signal S2(F) in consequence of the passage of the article across the second capacitive sensor (C2), which enables making the processing of the datum on the wholeness of the article independent of the effective orientation that this article has assumed during sliding thereof along the groove.

In fact, as is clearly illustrated in FIGS. 5A, 5B, 6A, 6B, thanks to the use of the two capacitive sensors (C1, C2) and in particular the way in which they are inserted and connected in the relative electronic circuits (O1, O2) at the respective reference potentials, if a whole article slides resting on a wall of the groove and passes across one of the two capacitive sensors at the armature connected to the reference potential, causing a perturbation in the signal which is comparable to the perturbation which a non-completely whole article might cause when passing resting on the other wall (the situation of FIGS. 5A and 5B), the whole article will always and in any case pass across the capacitive sensor at the armature which is not connected to the reference potential, thus causing a perturbation which is clearly distinguishable from those which the non-whole articles would cause (the situation of FIGS. 6A, 6B).

Figure 7:
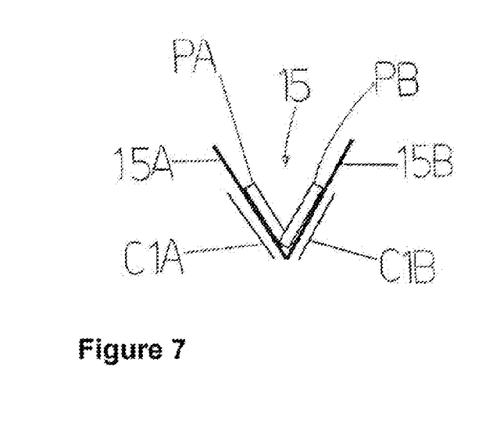
Figure 7A:
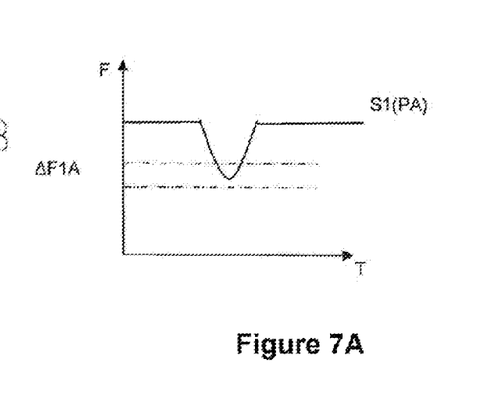
FIGS. 7A and 7B represent the progression of the output signal of the first circuit respectively in a case in which the article is inclined to the left or to the right, observing FIG. 7.
Figure 7B:
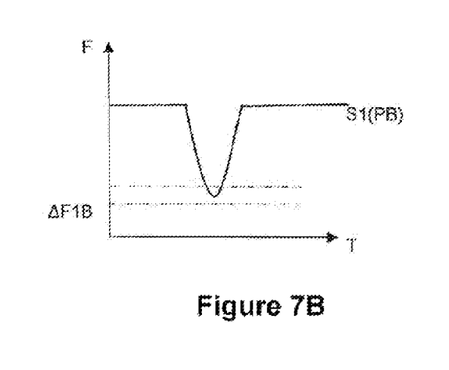
Figure 8:
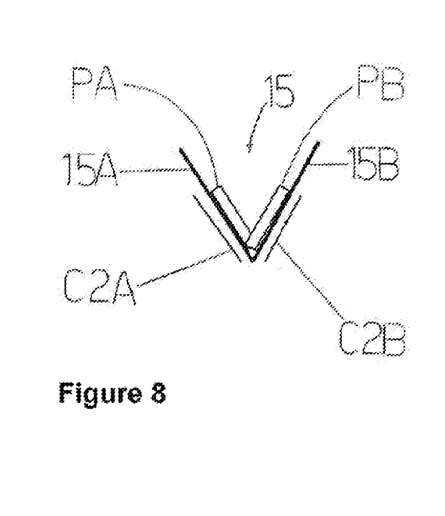
Figure 8A:
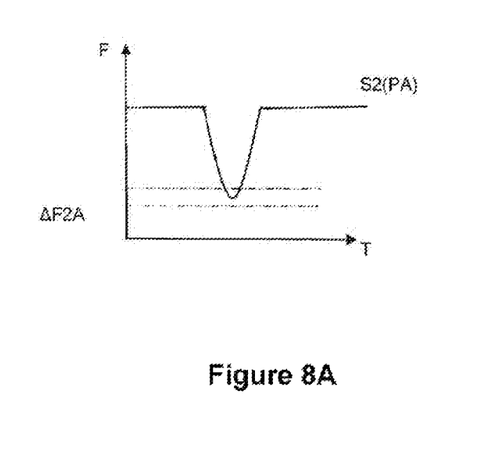
FIGS. 8A and 8B represent the progression of the output signal of the second circuit with respect to the case in which the article is inclined to the left or to the right, observing FIG. 8.
Figure 8B:
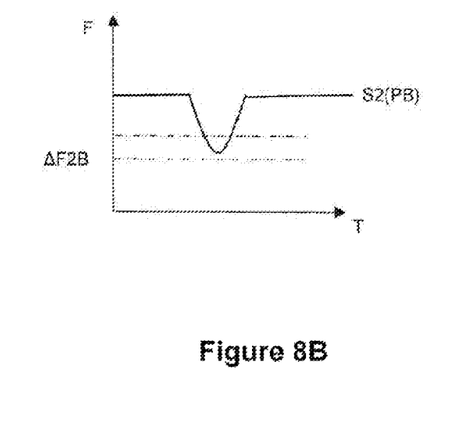

The determining of the values of the reference ranges for each of the two capacitive sensors indicating the whole articles is done according to the procedure illustrated in FIGS. 7, 7A, 7B; 8, 8A, 8B.

According to the type of articles to be inserted in the containers, a number of perfectly whole articles is selected, which articles correspond to the required standards and dimensions, shape and mass.

The articles the wholeness of which is known are made to slide one after another, and are distanced one from another, along the groove (15) of the sliding element (1) in such a way that only one of them at a time transits across the two capacitive sensors.

Statistically, a part of these articles will slide along the groove resting on the first lateral wall (15A) while another part of them will slide resting on the second lateral wall (15B).

Therefore, for each of the two capacitive sensors (C1, C2) it will be possible to determine a respective interval of wholeness according to whether the whole article has passed resting on the first lateral wall or on the second lateral wall.

For example, for the first capacitive sensor (C1) a reference range ΔF1A and a reference range ΔF1B can be determined, respectively for the data signals consequent to the sliding of the articles along the first lateral wall (15A) of the groove (15) and along the second lateral wall (15B).

In the same way, for the second capacitive sensor (C2) a reference range ΔF2A and a reference range ΔF2B can be determined, respectively for the data signals consequently to the sliding of the articles along the first lateral wall (15A) of the groove (15) and along the second lateral wall (15B).

In this way, when the device (100) is mounted and installed on the article packing machine, when the first signal S1(F) in outlet on the first circuit (O1), consequent to the passage of an article across the first capacitive sensor (C1) (of which the effective orientation is unknown) is such as to be out of both the reference range ΔF1A and the reference range ΔF1B, the processing unit (E) can immediately supply a datum indicating a non-whole article.

If, on the other hand, this first signal S1(F) in output from the first circuit (O1) falls internally of the reference interval ΔF1A or internally of the reference interval ΔF1B, the processing unit (E) will evaluate the second signal S2(F) provided in output from the second circuit (O2), consequent to the passage of the article across the second capacitive sensor (C2).

In this case, if also the second signal S2(F) falls within one of the two reference ranges, i.e. within the reference range ΔF2B or internally of the reference range ΔF2A, the processing unit (E) will supply a datum indicating a whole article, while in the opposite case it will supply a datum indicating a non-whole article.

Other characteristics of the device (100) of the present invention are set down in the following.

The device (100) comprises a first plate (21) and a second plate (22) (schematically visible in FIG. 5 and FIG. 6, the second plate also being denoted in a broken line in FIG. 4).

The first plate (21) is arranged externally of and parallel to the first lateral wall (15A) of the groove (15) while the second plate (22) is arranged externally of and parallel to the second lateral wall (15B) of the groove (15).

In this way, the first armature (C1A) of the first capacitive sensor (C1) and the first armature (C2A) of the second capacitive sensor (C2) can be arranged and mounted on the first plate (21) and the second armature (C1B) of the first capacitive sensor (C1) and the second armature (C2B) of the second capacitive sensor (C2) can be arranged and mounted on the second plate (22).

The sliding support (1) is arranged and positioned in such a way that the bottom of the groove (15) is inclined with respect to a horizontal plane by an angle comprised between 30° and 45°; in particular it is arranged such that the bottom of the groove (15) is inclined by an angle of 40%. This particular 40° inclination enables the articles coming from the vibrating conveyors (CV) to maintain, during the sliding thereof from the Inlet side (11) to the outlet side (12) of the sliding element (1), substantially the same reciprocal distance imposed on them by the vibrating conveyors (CV).

This guarantees that only an article at a time can transit across the two capacitive sensors.

The first lateral wall (15A) and the second lateral wall (15B) of the groove (15) of the sliding support (1) are realized in an electrically-insulating material at least at the zones where the armatures (C1A, C1B) of the first capacitive sensor (C1) and the armatures (C2A, C2B) of the second capacitive sensor (C2) are positioned.

The first electronic circuit (O1) and the second electronic circuit (O2) are as indicated above preferably two RC electronic oscillator circuits the diagrams of which are respective indicated In FIGS. 5 and 6 and are supplied such that the first reference potential Vref1 and the second reference potential Vref2 there is the same value, in particular supplied with a continuous tension of 5 Volts and the value of the first reference potential Vref1 and the value of the second reference potential Vref2 is 2.5 Volts.

The first armature (C1A) and the second armature (C1B) of the first capacitive sensor (C1) and the first armature (C2A) and the second armature (C2B) of the second capacitive sensor (C2) all have an isosceles trapezoid shape and are all arranged with the respect to the groove (15) in such a way that the smaller base of the isosceles trapeze is facing towards and parallel to the bottom of the groove (15) (see FIG. 4 in detail).

The device (100) can be realized in such a way that the sliding support (1) exhibits a number of article-sliding grooves (15) corresponding to the number of grooves present in the vibrating conveyors (CV) of the packing machines.

Consequently, the device (100) will have, for each of the grooves (15) of a first capacitive sensor (C1), with the first armature (C1A) thereof parallel to the first lateral wall (15A) of the groove (15) and the second armature (C1B) thereof parallel to the second lateral wall (15B) of the groove (15), a second capacitive sensor (C2), with the relative first armature (C2A) parallel to the first lateral wall (15A) of the groove (15) and the second armature (C2B) thereof parallel to the second lateral wall (15B) of the groove (15), a first electronic circuit (O1), preferably an oscillator, comprising the first capacitive sensor (C1) as a detecting component and a second electronic circuit (O2), preferably an oscillator, comprising the second capacitive sensor (C2) as a detecting component, where the first armature (C1A) of the first capacitive sensor (C1) of each of the grooves (15) is connected to a reference potential and the second armature (C2B) of the second capacitive sensor (C2) of each of the grooves (15) is connected to a respective second reference potential.

The device (100) of the present invention further exhibits the advantage, in the case of articles constituted by oblong tablets, with a pre-fracture line, of being able to discriminate and distinguish, contrarily to what occurs with the prior-art device of FIG. 1, those tablets which are broken along the pre-fracture line from perfectly-whole tablets.

In fact, the fact of having available two capacitive sensors which detect, one after another, the transit of a tablet from the first position (P1), where the first capacitive sensor (C1) is located, to the second position (P2), where the second capacitive sensor (C2) is located, enables the processing unit (E) to acquire, from the time taken by the tablet to complete the travel from the first capacitive sensor (C1) to the second capacitive sensor (C2), a datum relative to whether the oblong tablet is broken in half or is whole.

In fact, the time taken by an oblong tablet broken in half in the passage through the distance between the two capacitive sensors will be different (lower) than the time taken by a whole oblong tablet.

Definitively, the device (100) of the present invention enables detecting the effective wholeness of the articles independently of the effective orientation that they can assume once they have exited from the vibrating conveyors (CV) and consequently counting the number of articles recognized as whole.

Therefore, the use of this device (100) in automatic packing machines of pharmaceutical/parapharmaceutical articles internally of containers, guarantees that the containers can be filled always and only with effectively whole articles and with the exact number of articles required.

The above has been described by way of non-limiting example, and any eventual constructional variants are understood to fall within the scope of the following claims.

The invention claimed is:

1. A detecting and counting device for detecting a wholeness of and for counting pharmaceutical/parapharmaceutical articles, the device being usable in automatic machines for packing pharmaceutical/parapharmaceutical articles into containers, the automatic machines having vibrating conveyors (CV) for advancing the articles in line, distanced from one another, and a directing zone (W) for directing the articles towards the containers, for filling the containers, the device (100) comprising:

a sliding support (1) for sliding the articles, exhibiting an article inlet side (11) and an article outlet side (12), the sliding support (1) being positionable downstream of the vibrating conveyors (CV) and upstream of the article directing zone (W) in such a way that the article inlet side (11) is arranged consecutively to an outlet of the vibrating conveyors (CV), so as to receive therefrom one article after another, the article outlet side (12) facing towards an initial part of the directing zone (W), the sliding support (1) having at least one groove (15) along which the articles slide from the inlet side (11) to the outlet side (12), the at least one groove having a bottom, a first lateral wall (15A) and a second lateral wall (15B) and exhibiting a shape in transversal section that is such that the first lateral wall (15A) and the second lateral wall (15B) converge towards a bottom of the groove (15), a first capacitive sensor (C1) having a first armature (C1A) and a second armature (C1B), the first capacitive sensor (C1) being positioned with respect to the groove (15) in a first position (P1) and orientated in such a way that the first armature (C1A) is arranged parallel to the first lateral wall (15A) of the groove (15) and the second armature (C1B) is arranged parallel to the second lateral wall (15B) of the groove (15), a first electronic circuit (O1) connected to a first reference potential Vref1, the first capacitive sensor (C1) being a detecting component of the first circuit (O1) such that the first armature (C1A) of the first capacitive sensor (C1) is electrically connected to the first reference potential Vref1, the first circuit (O1) emitting a first signal S1(F) in output that is a function of the variation of the capacitive value of the first capacitive sensor (C1) following a transit of an article between the armatures thereof and indicating the shape of the article that has transited, a second capacitive sensor (C2) having a first armature (C2A) and a second armature (C2B), the second capacitive sensor (C2) being positioned with respect to the groove (15) in a second position (P2), located between the first position (P1) of the first capacitive sensor (C1) and the outlet side (12), and orientated in such a way that the first armature (C2A) is arranged parallel to the first lateral wall (15A) of the groove (15) and the second armature (15B) is arranged parallel to the second lateral wall (15B) of the groove (15), a second electronic circuit (O2) connected to a second reference potential Vref2, the second capacitive sensor (C2) being a detecting component of the second circuit (O2) such that the second armature (C2B) of the second capacitive sensor (C2), which is parallel to the second lateral wall (15B) of the groove (15), is electrically connected to the second reference potential Vref2, the second circuit (O2) emitting a second signal S2(F) in output that is a function of the variation of the capacitive value of the second capacitive sensor (C2) following transit of an article between the armatures and indicating the shape of the article that has transited, and, a data processing unit (E), connected to the first circuit (O1) and to the second circuit (O2) for receiving the first signal S1(F) and the second signal S2(F), the data processing unit (E) being configured to process the first signal S1(F) and the second signal S2(F) by singly comparing them to corresponding reference intervals indicative of whole articles, and supplying a datum relative to the wholeness of the article that has transited between the two capacitive sensors only when the first signal S1(F) and the second signal S2(F) both fall within the respective reference ranges.

2. The device of claim 1, further comprises a first plate (21) and a second plate (22), the first plate (21) being arranged externally of and parallel to the first lateral wall (15A) of the groove (15) and the second plate (22) being arranged externally of and parallel to the second lateral wall (15B) of the groove (15), and wherein the first armature (C1A) of the first capacitive sensor (C1) and the first armature (C2A) of the second capacitive sensor (C2) are arranged and mounted on the first plate (21) and the second armature (C1B) of the first capacitive sensor (C1) and the second armature (C2B) of the second capacitive sensor (C2) are arranged and mounted on the second plate (22).

3. The device of claim 2, wherein the sliding support (1) is arranged and positioned such that a bottom of the groove (15) is inclined with respect to a horizontal plane by an angle comprised between 30° and 45°.

4. The device of claim 2 wherein the sliding support (1) is arranged and positioned such that a bottom of the groove (15) is inclined by an angle of 40°.

5. The device of claim 3, wherein the first lateral wall (15A) and the second lateral wall (15B) of the groove (15) of the sliding support (1) are made of an electrically-insulating material at least in zones in which the first and second armatures (C1A, C1B) of the first capacitive sensor (C1) and the first and second armatures (C2A, C2B) of the second capacitive sensor (C2) are positioned.

6. The device of claim 2, wherein the first electronic circuit (O1) is an RC oscillating circuit and wherein the second electronic circuit (O2) is an RC oscillating circuit and wherein both the circuits (O1 O2) are supplied in such a way that the first reference potential Vref1 and the second reference potential Vref2 have the same value.

7. The device of claim 6, wherein the first oscillating circuit (O1) and the second oscillating circuit (O2) are supplied with a five volt tension and the value of the first reference value Vref1 and the value of the second reference potential Vref2 is 2.5 volts.

8. The device of claim 1, wherein the first armature (C1A) and the second armature (C1B) of the first capacitive sensor (C1) and the first armature (C2A) and the second armature (C2B) of the second capacitive sensor (C2) all have an isosceles trapezoid shape and are all arranged with the respect to the groove (15) such that a smaller base of the isosceles trapezoid is facing towards and parallel to the bottom of the groove (15).

9. The device of claim 1 wherein the sliding support (1) exhibits a number of article-sliding grooves (15) corresponding to a number of grooves present in the vibrating conveyors (CV) of the packing machines, and wherein each groove (15) has a first capacitive sensor (C1), with a first armature (C1A) thereof parallel to a first lateral wall (15A) of the groove (15) and a second armature (C18) thereof parallel to a second lateral wall (15B) of the groove (15), a second capacitive sensor (C2), with a first armature (C2A) parallel to the first lateral wall (15A) of the groove (15) and a second armature (C2B) thereof parallel to the second lateral wall (15B) of the groove (15), a first oscillating circuit (O1) using the first capacitive sensor (C1) as a detecting component and a second oscillating circuit (O2) using the second capacitive sensor (C2) as a detecting component, where the first armature (C1A) of the first capacitive sensor (C1) of each of the grooves (15) is connected to a reference potential and the second armature (C2B) of the second capacitive sensor (C2) of each of the grooves (15) is connected to a respective second reference potential.

\* \* \* \* \*